(12) United States Patent
Tokita et al.

(10) Patent No.: US 8,461,746 B2
(45) Date of Patent: Jun. 11, 2013

(54) LIQUID CONTROL APPARATUS

(75) Inventors: Toshinobu Tokita, Yokohama (JP); Kosuke Fujimoto, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 574 days.

(21) Appl. No.: 12/670,187

(22) PCT Filed: Jul. 24, 2008

(86) PCT No.: PCT/JP2008/063724
§ 371 (c)(1),
(2), (4) Date: Jan. 22, 2010

(87) PCT Pub. No.: WO2009/014261
PCT Pub. Date: Jan. 29, 2009

(65) Prior Publication Data
US 2010/0224274 A1    Sep. 9, 2010

(30) Foreign Application Priority Data

Jul. 25, 2007  (JP) ................................ 2007-193903

(51) Int. Cl.
*H01L 41/08* (2006.01)
(52) U.S. Cl.
USPC .......................................... 310/334; 310/311
(58) Field of Classification Search
USPC ............... 310/311, 313 R, 313 B, 313 D, 334
See application file for complete search history.

(56) References Cited

U.S. PATENT DOCUMENTS

| | | | |
|---|---|---|---|
| 6,244,738 B1 * | 6/2001 | Yasuda et al. ................. | 366/114 |
| 6,331,747 B2 * | 12/2001 | Yoshida et al. ........... | 310/313 R |
| 6,669,454 B2 | 12/2003 | Lal et al. | |
| 6,674,217 B1 | 1/2004 | Fujimoto ................. | 310/323.06 |
| 2001/0055529 A1 * | 12/2001 | Wixforth ........................ | 417/53 |
| 2004/0072366 A1 * | 4/2004 | Wixforth et al. .............. | 436/180 |
| 2004/0256951 A1 | 12/2004 | Fujimoto et al. .............. | 310/317 |

(Continued)

FOREIGN PATENT DOCUMENTS

| | | |
|---|---|---|
| JP | 2001-045774 | 2/2001 |
| JP | 2004-340820 | 12/2004 |

(Continued)

OTHER PUBLICATIONS

N. T. Nguyen, "MEMS-Micropumps: A Review", Journal of Fluids Engineering, Transactions of the ASME, vol. 124, pp. 384-392 (Jun. 2002).

(Continued)

*Primary Examiner* — Mark Budd
(74) *Attorney, Agent, or Firm* — Fitzpatrick, Cella, Harper & Scinto

(57) ABSTRACT

A liquid control apparatus controls movement of liquid in a microfluidic device having a sample introducing port, a sample delivering port, and a flow channel for holding liquid. The apparatus includes a vibration wave generating section for generating a vibration wave to be applied to the microfluidic device, and a signal supplying section for supplying drive signals so as to make the vibration wave generating section oscillate in different oscillation modes. The signal supplying section is capable of generating drive signals in a plurality of drive signal supply modes for realizing at least three of a transfer mode for moving liquid in a predetermined direction, a stop mode for stopping the movement of liquid, a mixing and/or agitation mode for mixing and/or agitating liquid, and a localization mode for localizing a predetermined substance in liquid, and for supplying the drive signals to the vibration wave generating section in a selected supply mode. In addition, the microfluidic device is held on the vibration wave generating section, and the transfer mode is carried out by using a resonance frequency to cause the microfluidic device to resonate.

3 Claims, 6 Drawing Sheets

U.S. PATENT DOCUMENTS

2006/0078473 A1 4/2006 Murakami .................. 422/100
2009/0129981 A1 5/2009 Tokita et al.

FOREIGN PATENT DOCUMENTS

| JP | 2005-164549 A | 6/2005 |
|---|---|---|
| JP | 2005-269821 | 9/2005 |
| WO | WO 2007/066478 | 6/2007 |

OTHER PUBLICATIONS

International Search Report and Written Opinion dated Oct. 21, 2008, in related corresponding PCT Japanese Patent Appln. No. PCT/JP2008/063724.

* cited by examiner

PHASE RELATION OF AMPLITUDE MODULATION AND SIGNAL ALONG WITH DEFORMATION OF WALL SURFACE

LIQUID CONTROL APPARATUS

TECHNICAL FIELD

This invention relates to a liquid control apparatus for a microfluidic device.

BACKGROUND ART

One of the regions in the field of MEMS (micro electromechanical systems) attracting attention includes bio-science, environment analysis and chemical synthesis. Devices referred to as microfluidic devices and µTAS (micro total analysis systems) are known as tools useful for such a region. A microfluidic device is prepared by forming a flow channel on a substrate of semiconductor, glass, ceramic or plastic materials and test samples, reagents or materials for chemical synthesis are made to flow through the flow channel of such a microfluidic device for the purpose of analysis or chemical synthesis. Development of devices that can exploit the advantages of microscale including a reduced consumption rate of solvent, sample and reagent and a high reaction speed if compared with conventional analysis techniques and batch processes and of apparatus/systems using such devices, is expected.

Japanese Patent Application Laid-Open No. 2004-340820 discloses a microfluidic device of a conventional type designed to employ an ultrasonic wave for transferring liquid and also for mixing/agitating liquid.

The microfluidic device disclosed in Japanese Patent Application Laid-Open No. 2004-340820 has a cross-sectional structure as illustrated in FIG. 6. Referring to FIG. 6, an ultrasonic platform type micro-chemical analysis system 100 includes a common platform 113 having a signal control circuit layer 111 and a transducer layer 112 and a transparent flow type microchip 114 arranged on the common platform 113. A flow channel 115 for transferring a sample or a reagent is formed in the inside of the flow type microchip 114 and ultrasonic transducers 116 are provided for the purpose of transferring and mixing/agitating a sample or a reagent in the flow channel 115. FIG. 6 is a cross-sectional view of a platform type micro-chemical analysis system 100 and hence ultrasonic transducers 116 seem to be arranged only one-dimensionally. However, ultrasonic transducers 116 are actually arranged in the form of a matrix. The ultrasonic transducers 116 arranged in the form of a matrix include liquid transferring transducers that are driven to operate along the flow channel 115 and mixing/agitation transducers that are arranged at a central part of the flow channel 115 in order to exploit their functional features.

However, the ultrasonic platform type micro-chemical analysis system disclosed in Japanese Patent Application Laid-Open No. 2004-340820 is accompanied by the following problems. Ultrasonic transducers 116 are arranged in the form of a matrix in the ultrasonic platform type micro-chemical analysis system according to Japanese Patent Application Laid-Open No. 2004-340820 and hence a large number of ultrasonic transducers 116 are required for the purpose of transferring and mixing/agitating liquid. Then, signals are applied to the ultrasonic transducers 116 for oscillations by means of respective signal generators and amplifiers. In other words, signal generators and amplifiers as many as the ultrasonic transducers 116 are required. Then, the apparatus/system for handling the platform type micro-chemical analysis system 100 is inevitably large and can involve high cost.

Additionally, the ultrasonic transducers 116 include liquid transferring transducers and mixing/agitation transducers that are different from each other. Thus, not only the apparatus/system can have large dimensions and involve high cost but also the platform type micro-chemical analysis system 100 per se can have large dimensions.

DISCLOSURE OF THE INVENTION

In view of the above-identified circumstances, an object of the present invention is to provide at low cost a compact liquid control apparatus that can control the vibration mode for the liquid existing in the flow channel in a microfluidic device by controlling the oscillation signal of the vibration wave generating section so as to realize a plurality of modes such as liquid transfer, mixing and/or agitation and localizing the sample in liquid.

Another object of the present invention is to provide a liquid control apparatus that can improve the efficiency of transferring liquid and that of mixing and/or agitation by arranging a valve in the flow channel in a microfluidic device.

According to the present invention, the above objects and other objects of the invention are achieved by providing a liquid control apparatus for controlling movement of liquid in a microfluidic device having a flow channel for holding liquid, comprising:

a vibration wave generating section for generating a vibration wave to be applied to the microfluidic device; and a signal supplying section for supplying drive signals so as to make the vibration wave generating section oscillate in different vibration modes;

wherein the signal supplying section is capable of generating drive signals in a plurality of drive signal supply modes for realizing at least three of:

a transfer mode for moving liquid in a predetermined direction;

a stop mode for stopping the movement of liquid;

a mixing and/or agitation mode for mixing and/or agitating liquid; and a localization mode for localizing a predetermined substance in liquid, and supplying the drive signals to the vibration wave generating section in a selected supply mode.

Preferably, a valve is provided in the flow channel of the microfluidic device.

Thus, the present invention can provide at low cost a compact liquid control apparatus that can control the vibration mode for liquid existing in the flow channel of a microfluidic device by means of oscillation signals supplied to the vibration generating section so that the liquid can be transferred or mixed and/or agitated or the sample in the liquid can be localized.

Additionally, the present invention can provide a liquid control apparatus that can further improve the efficiency of transferring or mixing and/or agitating the liquid by providing a valve at the flow channel in the microfluidic device.

Further features of the present invention will become apparent from the following description of exemplary embodiments with reference to the attached drawings.

BEST MODES FOR CARRYING OUT THE INVENTION

Figure 1:
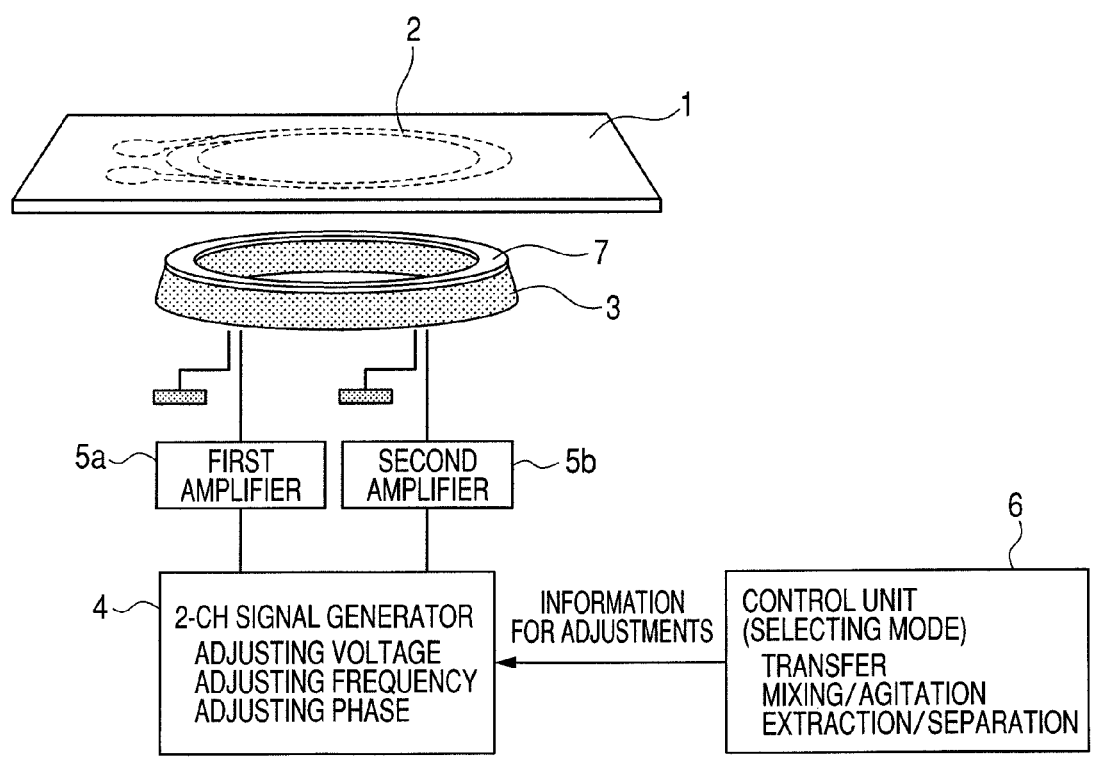
FIG. 1 is a schematic illustration of an embodiment of a liquid control apparatus according to the present invention.

A liquid control apparatus according to the present invention for controlling the movement of liquid in a microfluidic device having a flow channel for holding liquid has a vibration wave generating section for generating a vibration wave to be applied to the microfluidic device and a signal supplying section for supplying drive signals so as to make the vibration wave generating section oscillate in different oscillation modes. The signal supplying section is capable of generating drive signals in a plurality of drive signal supply modes for realizing at least three modes selected from a transfer mode for moving liquid in a predetermined direction, a stop mode for stopping the movement of liquid, a mixing/agitation mode for mixing/agitating liquid, and a localization mode for localizing a predetermined substance in liquid, and then supplying the drive signals to the vibration wave generating section in a selected supply mode.

Preferably, the vibration wave generating section includes as drive source a vibrator having a plurality of electro-mechanical energy conversion elements. More preferably, the vibration wave generating section includes an ultrasonic vibrator. Preferably, the ultrasonic vibrator has a laminated structure formed of a first piezoelectric element and a second piezoelectric element bonding to each other.

Preferably, the signal supplying section includes a signal generator for generating sinusoidal wave signals of two phases with controlled voltages, phases and frequencies as drive signals and an amplifier for amplifying the drive signals output from the signal generator.

Preferably, the signal supplying section has a control unit for controlling the signals output from the signal generator. The control unit includes a step managing section programmed to output information on operating steps, a mode selecting section for selecting one mode from a transfer mode of transferring liquid in a microfluidic device, a stop mode of stopping the transfer of the liquid, a mixing and/or agitation mode of mixing and/or agitating the liquid and a localization mode that is a pre-stage for separating the sample in the liquid based on the step information output from the step managing section, and an oscillation condition determining section for determining oscillation conditions of the ultrasonic vibrator according to the selected mode.

Preferably, the stop mode is at least either a mode for lowering the voltages of the two phase drive signals or a mode for altering the frequencies of the two phase drive signals to a frequency remarkably deviated from a resonance frequency of the microfluidic device.

Preferably, the transfer mode is a mode for setting the two phase drive signals to have a resonance frequency of the microfluidic device and controlling the two phases of the drive signals so as to make the ultrasonic vibrator oscillate for a traveling wave of amplitude modulation.

The mixing and/or agitation mode is at least either a mode for setting the two phase drive signals to have a resonance frequency of making the microfluidic device resonate and controlling the two phase drive signals to have a voltage smaller than the voltages in the transfer mode so as to make the drive signals have an oscillation amplitude smaller than the oscillation amplitude in the transfer mode or a mode for setting the two phase drive signals to have a frequency deviated from a resonance frequency of the microfluidic device.

Preferably, the mixing and/or agitation mode is a mode for setting the two phase drive signals to have a resonance frequency of the microfluidic device and switching the two phase drive signals to have an alternating phase difference so as to make the ultrasonic vibrator oscillate for a traveling wave of amplitude modulation moving alternately in opposite directions.

Preferably, the localization mode is at least either a mode for setting the two phase drive signals to have a resonance frequency of the microfluidic device and setting the two phase drive signals in sinusoidal waveform output from the signal generator to have no difference in time phase so as to make the ultrasonic vibrator oscillate for a standing wave of amplitude modulation or a mode for nullifying either output of the two phases of the drive signals in sinusoidal waveform.

Preferably, a liquid control apparatus according to the present invention is provided with a valve in the flow channel of the microfluidic device and further has a unit for controlling the two phases of the drive signals so as to open the valve in the transfer mode and make the ultrasonic vibrator oscillate for a traveling wave of amplitude modulation.

Preferably, a liquid control apparatus according to the present invention is provided with a valve in the flow channel of the microfluidic device and further has a unit for controlling the two phases of the drive signals so as to close the valve in the mixing and/or agitation mode and make the ultrasonic vibrator oscillate for a traveling wave of amplitude modulation.

Preferably, a liquid control apparatus according to the present invention is provided with a valve in the flow channel of the microfluidic device and further has a unit for controlling the valve so as to be opened and closed synchronously with a phase difference from the two phase drive signals from the signal generator, in the transfer mode.

For the purpose of the present invention, a liquid sample containing DNA is employed for a genetic examination and a liquid sample taken from a river is employed for looking into the contamination of the river. There are no limitations to samples to be used for the purpose of the present invention so long as the sample liquid is not extremely viscous and cannot be transferred by means of a liquid control apparatus according to the present invention.

For the purpose of the present invention, the term of "mode" is employed to classify the features and the operations of a liquid control apparatus according to the present invention. Examples of the use of the term of "mode" include a transfer mode, a mixing and/or agitation mode and a localization mode.

A liquid control apparatus according to the present invention can be downsized and manufactured at low cost because a sample in liquid can be transferred, mixed and/or agitated and localized by means of a oscillation signal of two phases. Additionally, the microfluidic device can also be downsized because the sample in liquid can be transferred, mixed and/or agitated and localized in the flow channel of the microfluidic device.

Now, a liquid control apparatus according to the present invention will be described in greater detail below by way of embodiments.

(First Embodiment)

The first embodiment of the present invention will be described below by referring to FIG. 1.

FIG. 1 is a schematic illustration of an example of liquid control apparatus according to the present invention. In FIG. 1, reference symbol 1 denotes a microfluidic device. A flow channel 2 is formed in the microfluidic device 1. The flow channel 2 serves to transfer a sample or a reagent, mix and/or agitate the sample or the reagent and separate the sample in a solution. In FIG. 1, numeral 3 denotes an ultrasonic stator that operates as vibration wave generating section and is typically formed by using the ring stator of an ultrasonic motor. In FIG. 1, numeral 4 denotes a signal generator and 5a and 5b denote respective amplifiers. Signal generated in the signal generator 4 is amplified by the amplifiers 5a and 5b and the amplified voltage signals are applied to the ultrasonic stator 3 in order to oscillate the ultrasonic stator 3. The ultrasonic stator 3 is equipped with a holding section 7 for holding part of the flow channel of the microfluidic device 1 disposed vis-à-vis the ultrasonic stator 3.

The ultrasonic stator 3 that operates as vibration wave generating section may be a three-phase stator or a linear stator so long as the ultrasonic stator has two or more than two vibration wave generation phases.

U.S. Patent Application Publication No. US-2004-0256951 discloses a specific configuration of ultrasonic stator, which may be adopted for the purpose of the present invention.

Normally, the signal generator 4 outputs sinusoidal waveform signals with a frequency that makes the ultrasonic stator 3 resonate in a condition where the ultrasonic stator 3 holds the microfluidic device 1 by means of the holding section 7 and the signal is amplified by an amplifier 5 (5a and 5b) to oscillate the ultrasonic stator 3. More specifically, the ultrasonic stator 3 has an oscillation source of two phases formed by piezoelectric elements arranged in its structure. Thus, the signal generator 4 generates two sinusoidal waveform signals with the same frequency by way of two channels and the signals of the two channels are amplified by the respective amplifiers 5 (the first amplifier 5a and the second amplifier 5b). When the ultrasonic stator 3 oscillates for a standing wave, either of the signals of the two channels generated by the signal generator 4 may be output in sinusoidal waveform or, alternatively, the sinusoidal waveform signals of the two channels may be made to be temporarily in phase and have the same frequency. When, on the other hand, the ultrasonic stator 3 oscillates for a traveling wave of amplitude modulation, the sinusoidal waveform signals of the two channels may be made to have the same frequency and show a phase difference, which may typically be 90°. The control unit 6 controls the switching operation and also operates as a signal supplying section for supplying drive signals for vibrating the vibration wave generating section.

The control unit 6 operates for mode selection of selecting a mode from four modes including a stop mode for stopping the liquid, a transfer mode, a mixing and/or agitation mode, and a localization mode that is a pre-stage for extracting and separating the sample, or the object of reaction.

The oscillation of the ultrasonic stator 3 is stopped in a stop mode. At this time, the output of the channel of either the signal generator 4 or the amplifier 5 is nullified. A technique of lowering the output of the signal generator 4 is also effective. Alternatively, a frequency that is remarkably deviated from the resonance frequency in a condition where the holding section 7 holds the microfluidic device 1 may be set.

(Transfer Mode)

The ultrasonic stator 3 oscillates for a traveling wave of amplitude modulation in the transfer mode. Since the liquid in the flow channel 2 is transferred in the moving direction of the traveling wave of amplitude modulation, the phase difference of the two phases is adjusted so as to make the traveling wave of amplitude modulation oscillate in the direction in which the liquid is driven to flow. The input voltage that determines the amplitude of oscillation of the ultrasonic stator 3 is preferably as high as possible within the range of not generating cavitation in the liquid in the flow channel 2. Additionally, the frequency preferably makes the ultrasonic stator 3 resonate in a condition where the holding section 7 holds the microfluidic device 1.

Figure 2A:
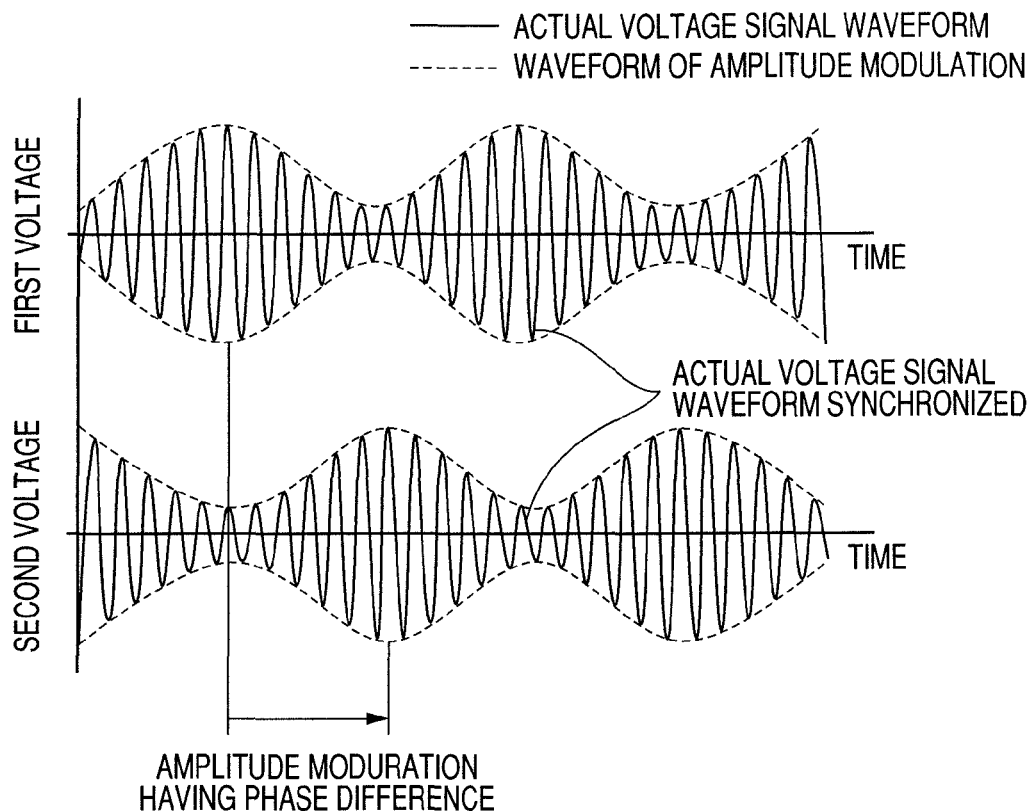
FIG. 2A is a schematic illustration of the phase relationship of signals for realizing a liquid transfer by amplitude modulation.

The liquid can be transferred more efficiently by using two signal waveforms as illustrated in FIG. 2A. This will be described below in detail.

FIG. 2A illustrates the voltage signal waveforms of two channels that the signal generator 4 generates in the transfer mode. The signals of the two channels are output as voltage signals subjected to periodical amplitude modulation (AM).

Figure 2B:
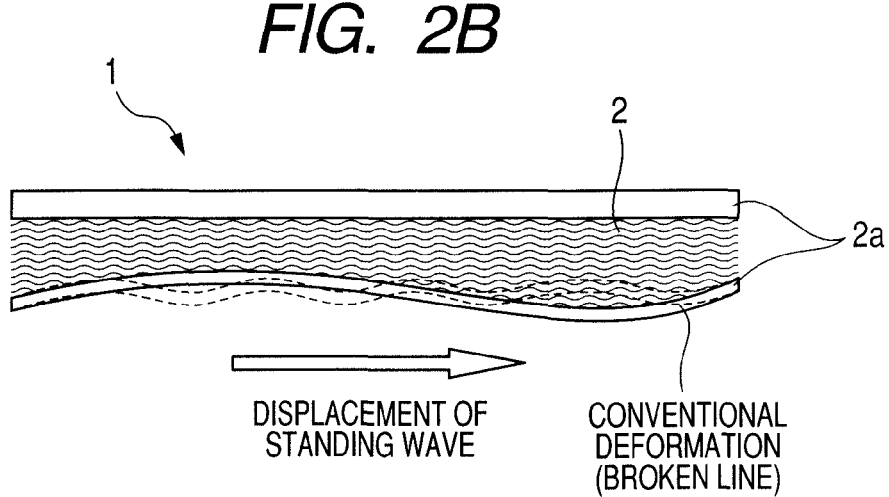
FIG. 2B is a schematic illustration of the corresponding wall deformation.

In FIG. 2A, the horizontal axes indicates time and the vertical axis indicates voltage signals, while the solid lines show the actual voltage signal waveforms and the broken lines show the waveforms of the modulated voltage signals. As illustrated in FIG. 2A, while the signals of the two channels have the same frequency and their phases are synchronized, a phase difference is provided for amplitude modulation. More specifically, it is seen from FIG. 2A that the first phase of amplitude modulation and the second phase of amplitude modulation show a phase difference of 90°. With this arrangement, the vibration wave generated in the ultrasonic stator 3 can give rise to a traveling wave of amplitude modulation as the displacement of the maximum amplitude of the standing wave generated by the synchronized two signals moves in a direction. As illustrated in FIG. 2B, the deformation of the flow channel wall 2a, or the wall surface of the flow channel 2 of the microfluidic device 1, can be moved in a predetermined direction with a low frequency that is a function of the period of amplitude modulation if compared with a conventional deformation indicated by a broken line. As the deformation of the wall surface travels, the liquid in the flow channel is pushed in the traveling direction so that consequently the liquid moves. The lower wall part of the flow channel wall 2a operates as the holding section 7 held by the ultrasonic stator 3. While the upper wall part of the flow channel wall 2a is illustrated as a fixed wall part, the present invention is by no means limited thereto and may alternatively be deformed as vibration is transmitted from the ultrasonic stator (not illustrated).

Now, the control of the flow rate or flow velocity will be described below. The flow rate or flow velocity changes due to the moving speed or the frequency of the generated traveling wave or the amplitude of the traveling wave.

In this embodiment, the frequency of amplitude modulation and the drive voltage (average amplitude) may be adjusted in order to control the moving speed and the frequency of the traveling wave according to the flow rate or flow velocity required for transferring the liquid.

Typically, the voltage signals supplied to the ultrasonic stator may show a voltage signal value of 10 to 200 V and the frequency of the ultrasonic signal may be 10 to 1 MHz, while the frequency of amplitude modulation may be 10 to 1,000 Hz and the modulation voltage of amplitude modulation (the displacement difference of maximum amplitude) may be 10 to 200 V.

More preferably, the voltage signal value may be 20 to 50 V and the frequency of the ultrasonic signal may be 20 to 100 KHz, while the frequency of amplitude modulation may be 50 to 500 Hz and the modulation voltage of amplitude modulation may be 5 to 50 V.

As signals illustrated in FIGS. 2A and 2B are generated with an arrangement as illustrated in FIG. 1, a standing wave that is deformed remarkably at an adjusted frequency can be moved to improve the efficiency of transferring liquid.

Additionally, since the liquid can be transferred highly efficiently by means of the two-channel signal generator 4, the apparatus/system can be downsized and manufactured at low cost.

(Mixing and/or Agitation Mode)

The ultrasonic stator 3 is oscillated as a traveling wave of amplitude modulation in the mixing and/or agitation mode. Note, however, that the input voltage is made lower than the input voltage in the transfer mode to reduce the rate of liquid transfer. The frequency is preferably such that the frequency makes the ultrasonic stator 3 resonate in a condition where the holding section 7 holds the microfluidic device 1 as in the transfer mode. Alternatively, the input voltage may be made equal to the input voltage in a transfer mode and the ultrasonic stator 3 may be made to oscillate at a frequency deviated from the frequency that makes the ultrasonic stator 3 resonate in a condition where the holding section 7 holds the microfluidic device 1. With either technique, the amplitude of oscillation of the ultrasonic stator 3 is smaller than in the transfer mode. Still alternatively, the amplitude of oscillation of the ultrasonic stator 3 may be made equal to the one in the transfer mode and the moving direction of the traveling wave of amplitude modulation may be switched at a short cycle. More specifically, the sign of the phase difference of the two channels is switched. For instance, the phase difference may be switched from 90° to −90° or vice versa.

(Localization Mode)

The ultrasonic stator 3 oscillates as a standing wave in the localization mode. Preferably, the frequency is such that the frequency makes the ultrasonic stator 3 resonate in a condition where the holding section 7 holds the microfluidic device 1. Then, the sample that is the object of reaction gathers at the nodes of the standing wave. In other words, the sample can be localized.

(Control Method in Each Mode)

Figure 3:
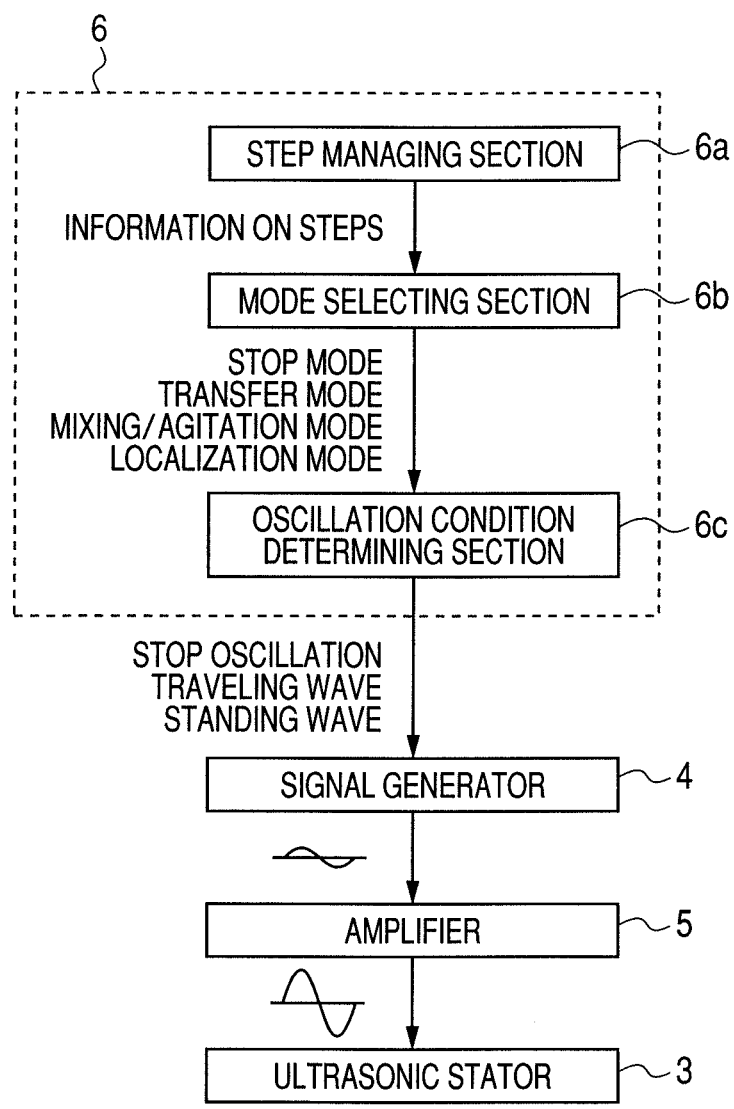
FIG. 3 is a schematic illustration of the flow of the sequence of the different steps of the first embodiment of the present invention.

Now, the steps from selecting a mode to outputting a signal will be described in detail by referring to FIG. 3. FIG. 3 is a schematic illustration of the flow of the sequence of the different steps of the first embodiment.

Referring to FIG. 3, numeral 6a denotes the step managing section. The step managing section 6a is programmed so as to conduct the steps appropriately in a chemical or biochemical process. The process may be injecting a sample, mixing a sample with a reagent put in a microfluidic device 1 in advance, extracting and refining a certain sample, causing them to react and detecting the reaction product and realizing a chemical synthesis. In FIG. 3, numeral 6b denotes a mode selecting section that operates as a signal supplying section. The mode selecting section 6b selects a mode out of the stop mode for stopping liquid, the transfer mode, the mixing and/or agitation mode, and the localization mode according to the step information from the step managing section 6a. Oscillation condition determining section 6c holds the conditions of oscillation of the ultrasonic stator 3 for realizing a supply mode and determines the supply mode that corresponds to the selected one of the above listed four modes. The oscillation condition determining section 6c then provides the signal generator 4 with information on the conditions of oscillation including the conditions for stopping oscillation and conditions for oscillating a traveling wave of amplitude modulation and a standing wave. The signal generator 4 outputs signals according to the information on the conditions of oscillation of the selected supply mode, and the signals are amplified by the amplifiers 5 so as to oscillate or stop the oscillation of the ultrasonic stator 3.

The techniques of transferring and mixing and/or agitating the liquid in the flow channel 2 of the microfluidic device 1 and localizing the sample in the liquid and the control unit 6 for controlling these operations of the first embodiment are described above. Additionally, operations of transferring and mixing and/or agitating the liquid and localizing the sample in the liquid by means of oscillation signals of two channels are also described above. Thus, this embodiment can downsize the entire apparatus/system so as to manufacture the apparatus/system at low cost. Still additionally, liquid can be transferred and mixed and/or agitated and a sample can be localized in the liquid in the flow channel 2 of a microfluidic device 1 so that the microfluidic device 1 can also be downsized.

While at least three of the above listed four modes need to be provided for the purpose of the present invention, preferably all the four modes are provided. If necessary, one or more than one other modes for realizing one or more than one additional steps (e.g., a step of checking defective microfluidic devices by applying a predetermined frequency) may be provided.

(Second Embodiment)

A technique of oscillating an ultrasonic stator 3 in a mixing and/or agitation mode with an amplitude smaller than, or a voltage lower than, in a transfer mode in order to oscillate the ultrasonic stator 3 as traveling wave of amplitude modulation is described above for the first embodiment. However, the liquid is transferred, if slightly, while the ultrasonic stator 3 is oscillated as traveling wave of amplitude modulation by means of a voltage, although the voltage is low. In the second embodiment, a valve is provided in the flow channel 2. This will be described below along with a method of controlling the valve.

Figure 4:
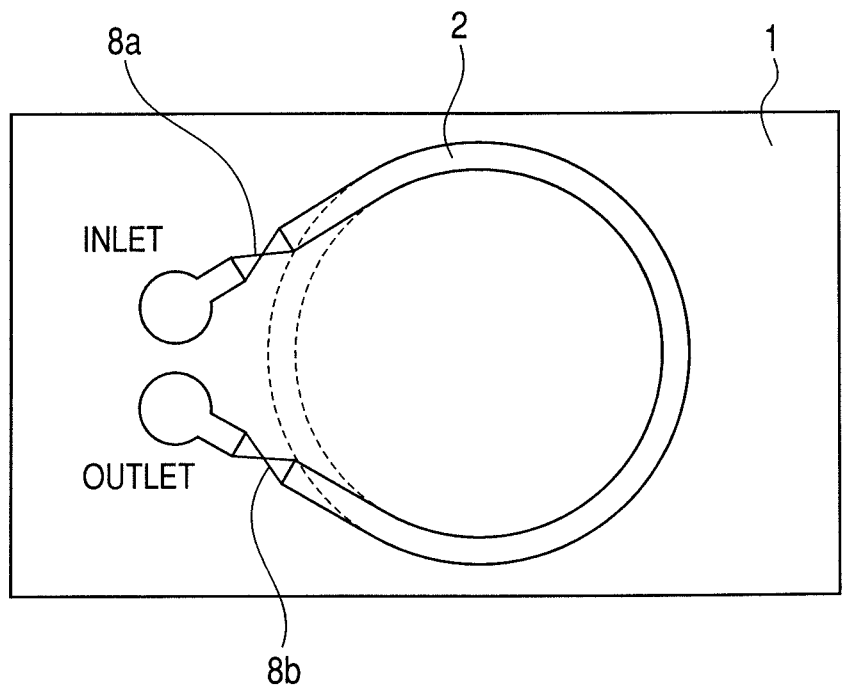
FIG. 4 is a schematic illustration of a microfluidic device applicable to the second embodiment and the third embodiment of the present invention.
Figure 5:
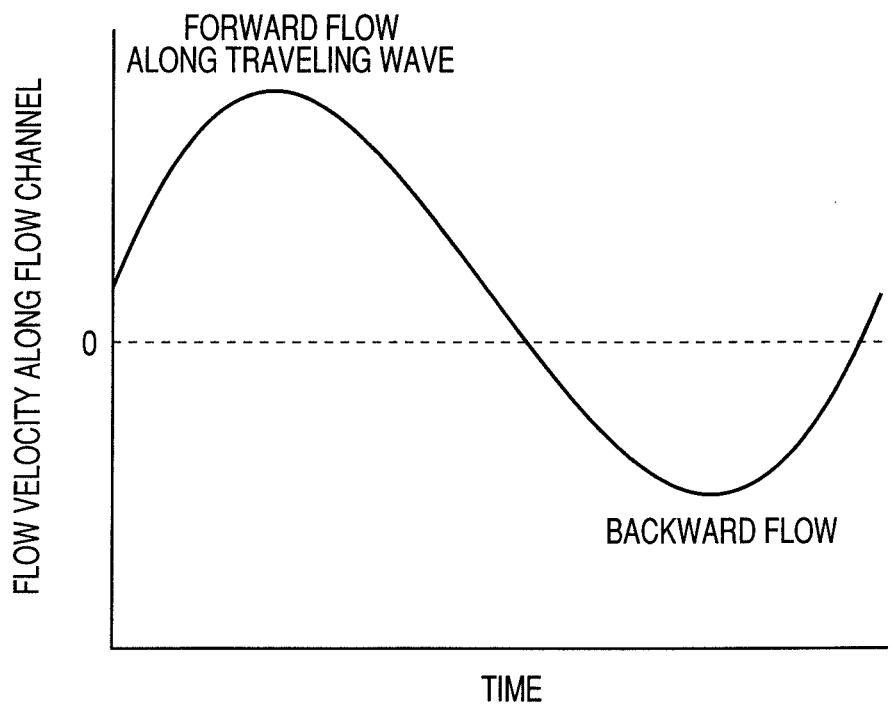
FIG. 5 is a schematic illustration of time history of the flow rate in a liquid transfer.
Figure 6:
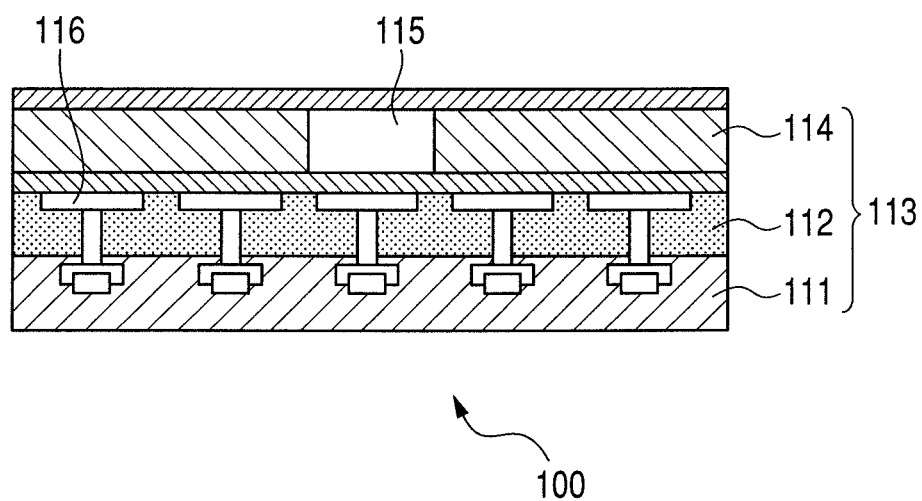
FIG. 6 is a schematic illustration of a known microfluidic device and a method of utilizing an ultrasonic wave for transferring liquid and also for mixing and/or agitating liquid.

Referring to FIG. 4, numeral 8 (8a and 8b) denotes respective valves. In other words, at least the sample introducing port side or the sample delivering port side of the flow channel 2 is provided with a valve 8. Then, a mode is selected from four modes including a stop mode, a transfer mode, a mixing and/or agitation mode and a localization mode that is a pre-stage for extracting and separating the sample, or the object of reaction by a control unit (not illustrated). The second embodiment will be described below only in terms of the difference between the first embodiment and the second embodiment.

In the transfer mode, the valve 8 is opened and the ultrasonic stator oscillates as a traveling wave of amplitude modulation moving from the sample introducing port side toward the sample delivering port side.

In the mixing and/or agitation mode, the valve 8 is closed and the ultrasonic stator oscillates as a traveling wave of amplitude modulation. Either moving direction may be selected in this mode. The input voltage may be the same as in a transfer mode. A frequency at which the ultrasonic stator resonates in a condition where the holding section 7 holds the microfluidic device 1 is preferably employed both in a transfer mode and in a mixing and/or agitation mode.

Both the stop mode and the localization mode are the same as those of the first embodiment and the valve 8 may be held opened or closed in these modes.

The operation of the valve 8 in the microfluidic device 1 is described above. Thus, with this embodiment, the valve 8 is closed in a mixing and agitation mode, no liquid is transferred in this mode and hence the efficiency of mixing and/or agitation in the flow channel 2 is improved.

(Third Embodiment)

Techniques for oscillating an ultrasonic stator as traveling wave of amplitude modulation in the direction of transferring liquid in a transfer mode are described above for both the first embodiment and the second embodiment. The liquid in the flow channel 2 flows in the moving direction of the traveling wave of amplitude modulation as the ultrasonic stator is oscillated. However, the liquid actually behave such that the liquid flows in the moving direction of the traveling wave of amplitude modulation, returns in the other way and then flows again in the moving direction of the traveling wave of amplitude modulation. In other words, the liquid flows slowly in average, constantly oscillating on the way. Therefore, the valve 8 of FIG. 4 is actively controlled for being opened and closed. More specifically, the valve 8 is opened in synchronism with the timing when the liquid flows from the sample introducing port side toward the sample delivery port side and closed in synchronism with the timing when the liquid flows from the sample delivering port side toward the sample introducing port side. To describe more plainly, the valve 8 is controlled so as to be synchronized out of phase of the signals from the signal generator.

Thus, with the third embodiment, the valve 8 is operated in a manner as described above in a transfer mode to improve the efficiency of transferring liquid.

Since a liquid control apparatus according to the present invention can transfer and mix and/or agitate the liquid existing in the flow channel of a microfluidic device and localize the sample in the liquid by means of oscillation signals of two phases, the liquid control apparatus can be utilized in an apparatus that requires accurate control of transfer of liquid such as μTAS.

Now, an example that proves the advantages of the present invention will be described below.

EXAMPLE 1

An apparatus having a configuration as illustrated in FIG. 1 was prepared. A flow channel was formed in a microfluidic device that was made of polymethyl methacrylate (PMMA). The flow channel was 0.5 mm high and 2 mm wide in cross section and the circular flow channel had a diameter of 76 mm as observed from the center of the cross section. Water was introduced into the flow channel by 0.238 ml. Voltage signals of 30 kHz were supplied in synchronism with the first and second phases to give rise to resonance and hence the frequency was found to be the resonance frequency. With the prepared arrangement, a resonance frequency of 30 kHz to 32 kHz can be set.

100 Hz was selected as frequency of amplitude modulation and the flow rate of the water was observed by means of PIV (particle image velocimetry). The moving speed of the traveling wave generated by the amplitude modulation of 100 Hz was determined to be 2.5 m/s by computations. 40 V was selected for the input voltage (Vcc). As a result, it was found that the water flows at an average flow rate of 10 mm/s.

A traveling wave of 31 kHz was applied to the first and second phases with an input voltage of 40 V without amplitude modulation. Then, the average flow rate was found to be about 1 mm/s.

In other words, two different transfer modes of different flow rates could be realized by means of the above described two different signals.

In a stop mode, the input voltage of the first and second voltage signals was changed from 40 V to 0 V. As a result the liquid in the flow channel stopped moving.

The liquid in the flow channel also stopped when the input frequency was changed from the resonance frequency of 31 kHz to 28 kHz or to 33 kHz.

A dispersion solution prepared by dispersing microparticles of a diameter of 300 μm in water was introduced into the flow channel to replace the water.

The signals of two channels are synchronized and a signal of 30 kHz was supplied to the first and second phases to produce a standing wave in a localization mode. Particles were visually observed to find that they were localized at regular intervals in the flow channel.

The traveling wave of 31 kHz of the signals of two channel was applied at 10 V in a mixing and/or agitation mode and the phase was inverted at every other second to visually find that the microparticles that had been localized were uniformly agitated.

Thus, four modes including a transfer mode, a stop mode, a mixing and/or agitation mode and a localization mode can be realized by controlling a drive signal, using an ultrasonic stator.

The present invention is not limited to the above embodiments and various changes and modifications can be made within the spirit and scope of the present invention. Therefore, to apprise the public of the scope of the present invention, the following claims are made.

This application claims the benefit of Japanese Patent Application No. 2007-193903, filed Jul. 25, 2007, which is hereby incorporated by reference herein in its entirety.

The invention claimed is:

1. A liquid control apparatus for controlling movement of liquid in a microfluidic device having a sample introducing port, a sample delivering port, and a flow channel for holding liquid, the flow channel being formed within the microfluidic device and communicating with the sample introducing port and the sample delivering port, the apparatus comprising:
   a vibration wave generating section for generating a vibration wave to be applied to the microfluidic device; and
   a signal supplying section for supplying drive signals so as to make the vibration wave generating section oscillate in different oscillation modes,
   wherein the signal supplying section is capable of generating drive signals in a plurality of drive signal supply modes for realizing at least three of:
   a transfer mode for moving liquid in a predetermined direction;
   a stop mode for stopping the movement of liquid;
   a mixing and/or agitation mode for mixing and/or agitating liquid; and
   a localization mode for localizing a predetermined substance in liquid, and for supplying the drive signals to the vibration wave generating section in a selected supply mode, and
   wherein the microfluidic device is secured to the vibration wave generating section, and the transfer mode is carried out using a resonance frequency to cause the microfluidic device to resonate.

2. A liquid controlling apparatus, comprising:

a microfluidic device having a sample introducing port, a sample delivering port, and a flow channel for holding liquid and in communication with the sample introducing port and the sample delivering port;

a vibration wave generating section for generating a vibration wave to be applied to the microfluidic device; and a signal supplying section for supplying drive signals so as to make the vibration wave generating section oscillate in different oscillation modes, wherein the signal supplying section is capable of generating drive signals in a plurality of drive signal supply modes for realizing at least three of:

a transfer mode for moving liquid in a predetermined direction;

a stop mode for stopping the movement of liquid;

a mixing and/or agitation mode for mixing and/or agitating liquid; and a localization mode for localizing a predetermined substance in liquid, and for supplying the drive signals to the vibration wave generating section in a selected supply mode, and wherein the microfluidic device is secured to the vibration wave generating section, and the transfer mode is carried out by using a resonance frequency to cause the microfluidic device to resonate.

3. A liquid controlling apparatus according to claim 2, wherein the vibration wave generating section is shaped to match the flow channel, and the resonance frequency causes a wall surface of the flow channel to move in a predetermined direction.

* * * * *